United States Patent
Williams

(10) Patent No.: US 6,481,264 B1
(45) Date of Patent: Nov. 19, 2002

(54) MATERIALS FOR SOLID-STATE GAS SENSORS

(75) Inventor: David Edward Williams, Abingdon (GB)

(73) Assignee: Capteur Sensors and Analysers Limited, Didcot (GB)

(*) Notice: Subject to any disclaimer, the term of this patent is extended or adjusted under 35 U.S.C. 154(b) by 0 days.

(21) Appl. No.: 09/830,132

(22) PCT Filed: Oct. 26, 1999

(86) PCT No.: PCT/GB99/03532

§ 371 (c)(1),
(2), (4) Date: Apr. 24, 2001

(87) PCT Pub. No.: WO00/24677

PCT Pub. Date: May 4, 2000

(30) Foreign Application Priority Data

Oct. 26, 1998 (GB) ................................ 9823428

(51) Int. Cl.$^7$ ......................... G01N 7/00; G01N 30/96; H01C 7/10
(52) U.S. Cl. ................ 73/31.06; 338/22 SD; 422/88
(58) Field of Search ............... 73/23, 2, 32, 31.06; 338/22 SD; 422/88, 98; 436/121, 151

(56) References Cited

U.S. PATENT DOCUMENTS

| | | | | |
|---|---|---|---|---|
| 4,579,751 A | * | 4/1986 | Forster | 427/595 |
| 5,497,139 A | * | 3/1996 | Takahashi et al. | 388/22 SD |
| 5,864,148 A | * | 1/1999 | Feltz et al. | 257/43 |
| 6,202,473 B1 | * | 3/2001 | Stokes | 73/31.06 |

FOREIGN PATENT DOCUMENTS

| | | | |
|---|---|---|---|
| DE | 26 03 785 | | 8/1977 |
| DE | 4402117 | * | 8/1995 ........... C04B/35/26 |
| EP | 0 759 552 A | | 2/1997 |
| JP | 409223602 | * | 8/1997 ............ H01C/7/04 |

OTHER PUBLICATIONS

XP002129198 Yang Xiaojuan Dec. 7, 1998; Chemical Abstract vol. 129, No. 23; abstract & Sci. China, Ser. B:Chem., vol. 41, No. 4, 1998, pp. 442–448.

XP000867534 Tridot: "Nouveau System De Thermopesee" Bulletin De La Societe Chimique De France, vol. 12, 1970, pp. 4304–4307, p. 4306.

* cited by examiner

Primary Examiner—Hezron Williams
Assistant Examiner—Jay L Politzer
(74) Attorney, Agent, or Firm—Woodcock Washburn LLP

(57) ABSTRACT

A sensor for detecting the presence of gas and methods for use. The sensor has a low sensitivity to relative humidity and high sensitivity to the presence of gases such as carbon monoxide. The sensor is comprised of ternary oxides of the formula $Cr_{2-x}(M1_zM2_{1-z})_xO_3$ with M1=Fe or Mn, M2=Fe, Mn, or Al, $0.005 \leq x \leq 1.95$, $0.005 \leq z \leq 0.995$; ternary oxides of the formula $Cr_{2-x}(M1_zM2_{1-z})_xO_3$ with M1=Fe or Mn, M2=Ti, $0.005 \leq x \leq 1.95$, $0.005 \leq z \leq 0.45$; or quaternary and quinternary oxides of the formula $Cr_{2-x}((M1_aM2_bM3_c)_zM4_{1-z})_xO_3$ with M1=Fe, M2=Mn, M3=Al, and M4=Ti, $0 \leq a,b,c \leq 1$, $0.005 \leq x \leq 1.95$, and $0.005 \leq z \leq 0.45$.

10 Claims, 9 Drawing Sheets 1000 ppm CO 10 ppm ETHANOL 100 ppm NH$_3$

95% HUMIDITY

MATERIALS FOR SOLID-STATE GAS SENSORS

This invention relates to solid-state compositions for use as gas sensors.

The composition $Cr_{2-x}Ti_xO_{3+y}$, with $0.005 \leq x \leq 0.45$, and where y is determined by the charge balance in the crystal lattice and the equilibrium of oxygen vacancies with oxygen gas in the ambient atmosphere, has been described as a gas sensitive resistor material having advantages of low sensitivity to relative humidity and high sensitivity to gases such as carbon monoxide. However, the effect of relative humidity change on this material is still too large to allow sensors manufactured using it to meet modern standards for carbon monoxide detectors for domestic use.

The present invention relates to compositions which have the advantage of an even lower sensitivity to relative humidity whilst retaining a high sensitivity to carbon monoxide.

The invention provides the following compositions:

binary oxides of the formula $Cr_{2-x}M_xO_3$ with M=Fe or Mn and $0.005 \leq x \leq 1.95$.

Ternary oxides of the formula $Cr_{2-x}(M1_zM2_{1-z})_xO_3$ with M1=Fe or Mn, M2=Fe, Mn or Al, $0.005 \leq x \leq 1.95$ and $0.005 \leq z \leq 0.995$;

ternary oxides of the formula $Cr_{2-x}(M1_zM2_{1-z})_xO_3$ with M1=Fe or Mn, M2=Ti and $0.005 \leq x \leq 1.95$, $0.005 \leq z \leq 0.45$;

quaternary and quinternary oxides of the formula $Cr_{2-x}((M1_aM2_bM3_c)_zM4_{1-z})_xO_3$ with M1=Fe, M2=Mn, M3=Al and M4=Ti, and $0 \leq a,b,c \leq 1$, $0.005 \leq x \leq 1.95$, and $0.005 \leq z \leq 0.45$.

Within these compositions, a very wide range of impurities, specifically including alkali and alkaline earth metals and transition metals, can be tolerated without degradation of the properties.

The invention also provides gas sensors incorporating these inventive compositions.

Preferred features of the invention will now be described with reference to the accompanying drawings, in which.

PREPARATION OF MATERIALS

Chromium titanium oxide powder was prepared using $Cr_2O_3$ made from the decomposition of ammonium dichromate. The powder was dispersed in isopropanol and a titanium isopropoxide solution in isopropanol was added while stirring under ultrasound. After the solvent was removed, the remaining powder was dried and fired at 1000° C. for 12 hours.

Chromium manganese oxide was prepared by mixing either $Mn_2O_3$ or $MnO_2$ and $Cr_2O_3$ with isopropanol in a ballmill for 12 hours. After removing the solvent, the power was fired at 1000° C. for 12 hours.

Chromium iron oxide was prepared similarly, but with $Fe_2O_3$ substituted for $Mn_2O_3$.

Chromium titanium manganese oxide and chromium titanium iron oxide were similarly prepared, but with chromium titanium oxide substituted for $Cr_2O_3$.

Chromium titanium aluminium oxide was similarly prepared using chromium titanium oxide and $Al_2O_3$.

X-ray diffraction analysis showed the chromium manganese oxide and chromium iron oxide to have a chromium oxide phase with a separate phase of some unreacted manganese or iron oxide.

By varying the proportions of mixed oxides, the stoichiometry of the final power can be controlled.

For the results shown in FIGS. 1 to 7 the electrical behaviour and the response to carbon oxide and water vapour was investigated by a computer controlled rig. For that, 1 gram of powder was pressed at 1 ton into approximately 2 mm thick pellets and clamped between gold foil electrodes inside a silica tube in a furnace. Up to 4 pellets could be investigated at the same time. The gas flowed horizontally through the rig. The gas concentration was controlled by regulating flow rates using mass flow controllers (Tylan). In the CO experiment dry purified laboratory air was mixed with "1% CO in air" gas (10000 ppm) obtained from BOC. The relative humidity of water at 20° C. was altered by mixing two air streams, one being dry, and the other being air saturated with water vapour at room temperature.

The following abbreviations are used in FIGS. 1 to 7:

| | |
|---|---|
| CTO | $Cr_{1.8}Ti_{0.2}O_3$ |
| CMO | $Cr_{1.8}Mn_{0.2}O_3$ |
| CFO | $Cr_{1.8}Fe_{0.2}O_3$ |
| CTMO | $Cr_{1.8}Ti_{0.1}Mn_{0.1}O_3$ |
| CTFO | $Cr_{1.8}Ti_{0.1}Fe_{0.1}O_3$ |

Figure 1:
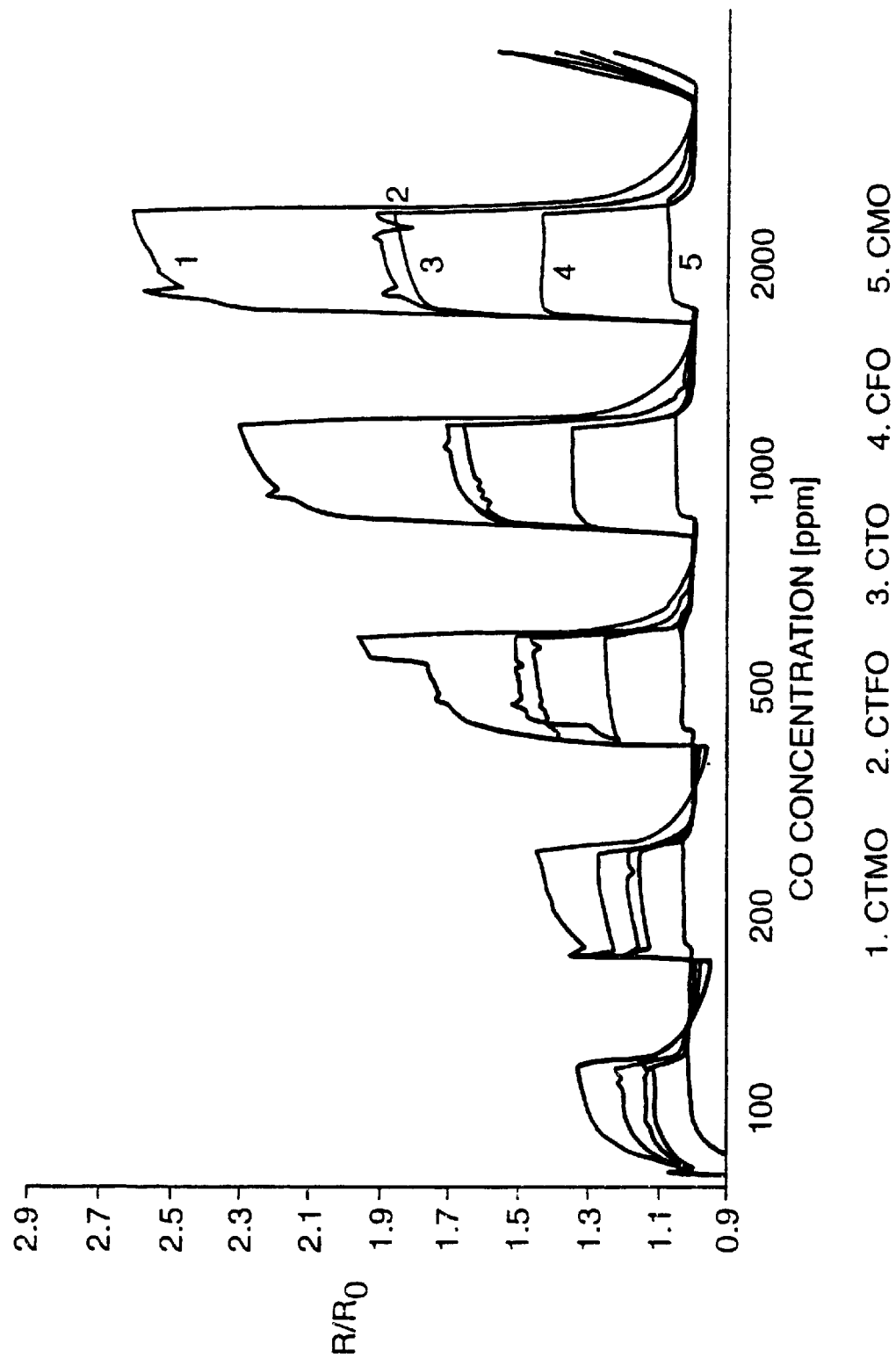
FIG. 1 is a graph showing the responses of various materials to carbon monoxide at 350° C.
Figure 2:
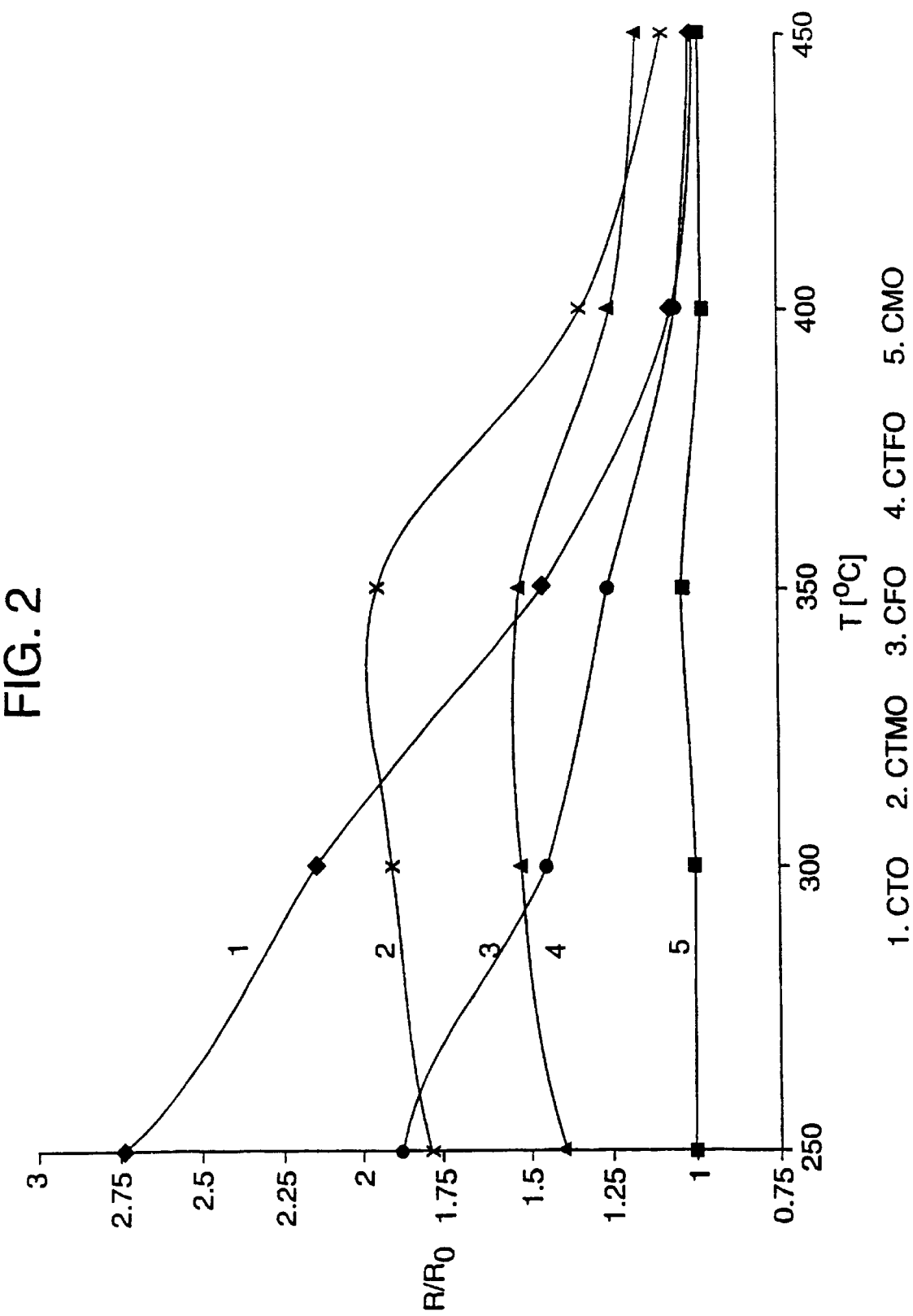
FIG. 2 is a graph showing the responses of various materials to 500 ppm carbon monoxide at various temperatures.
Figure 3:
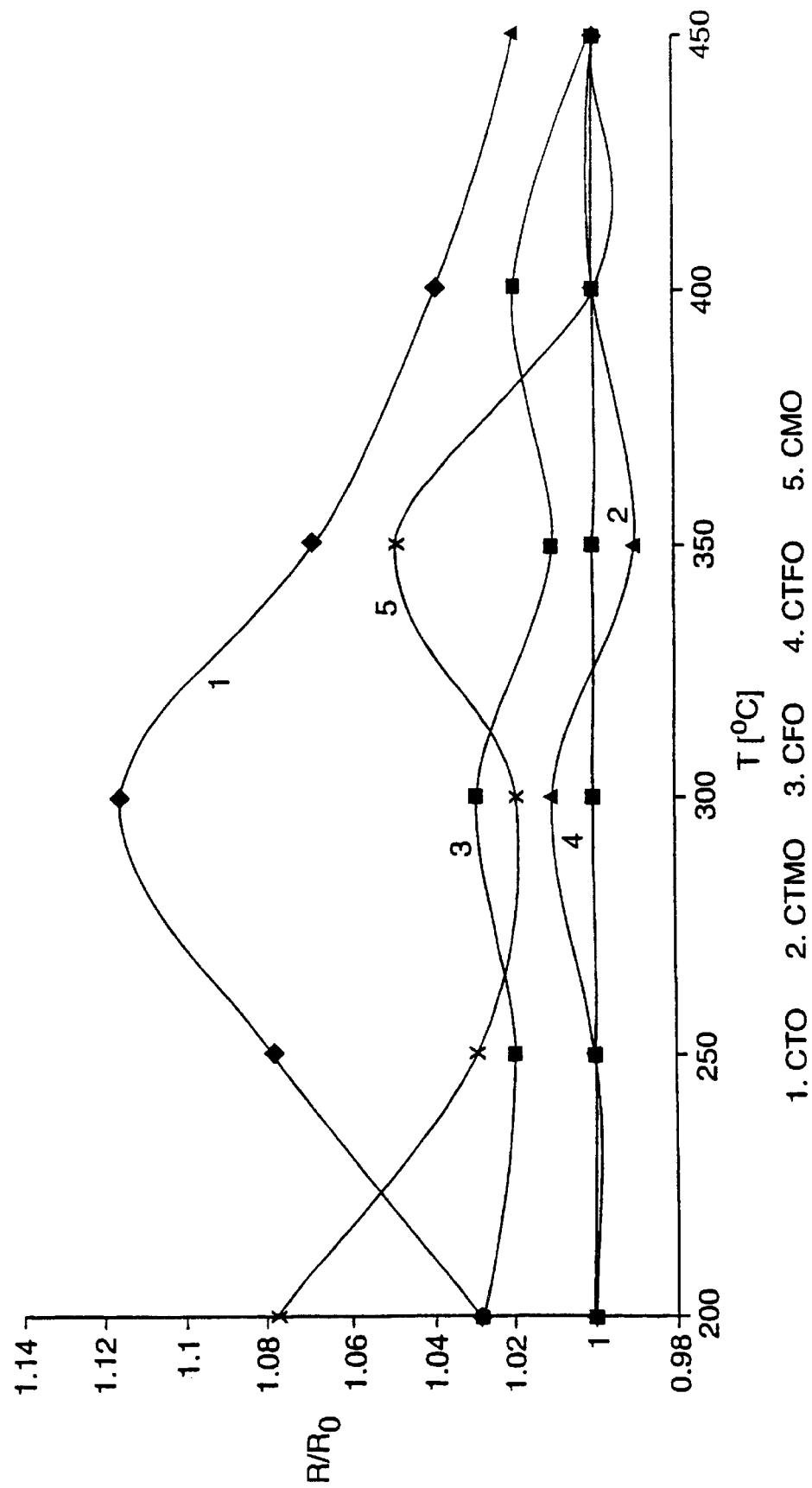
FIG. 3 is a graph showing the responses of various materials to water at 20% relative humidity (20° C.) at various temperatures.
Figure 4:
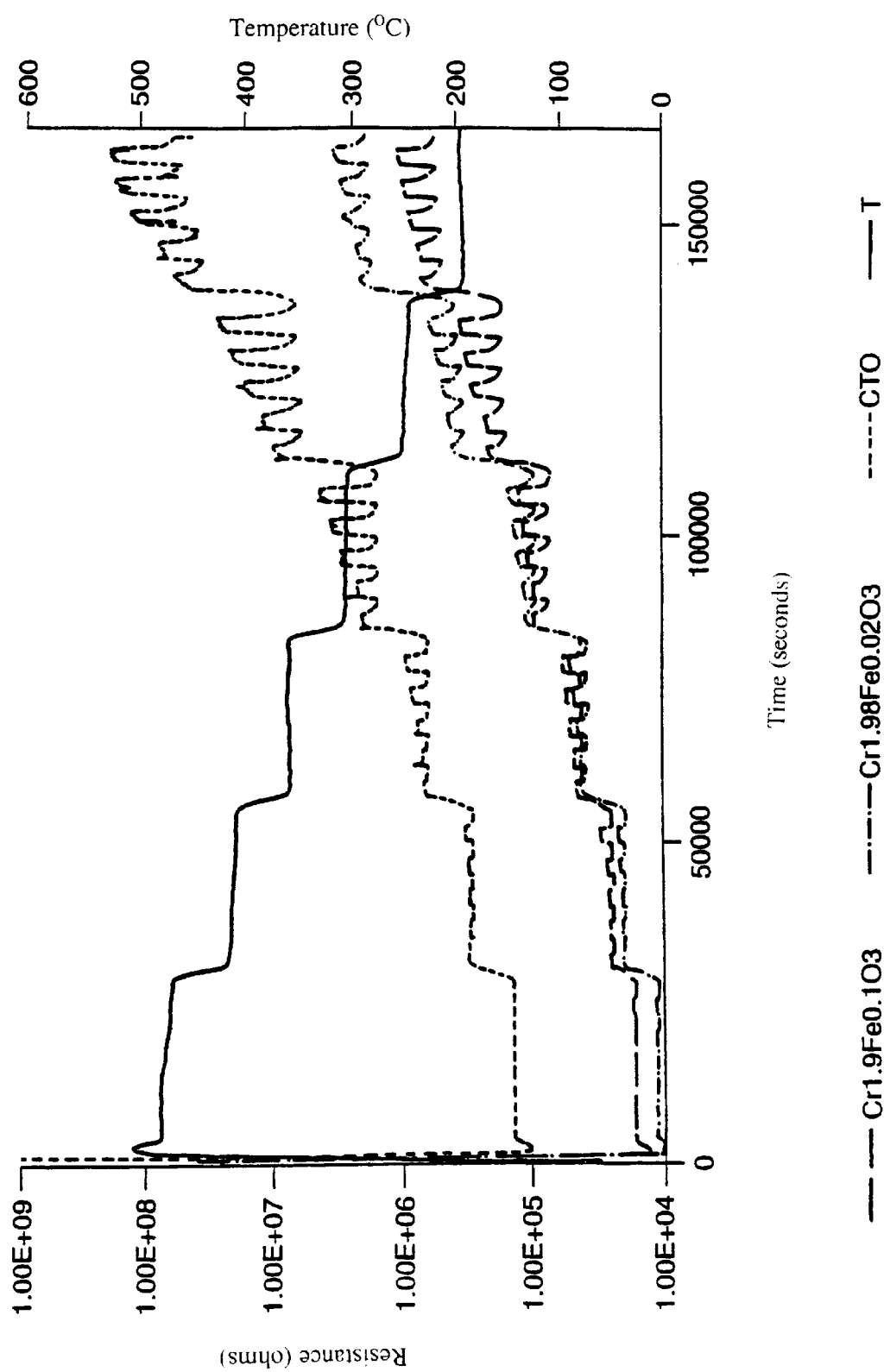
FIGS. 4 and 5 show the responses of chromium iron oxide and chromium titanium oxide to CO at various concentrations, and water at various relative humidities, respectively.
Figure 5:
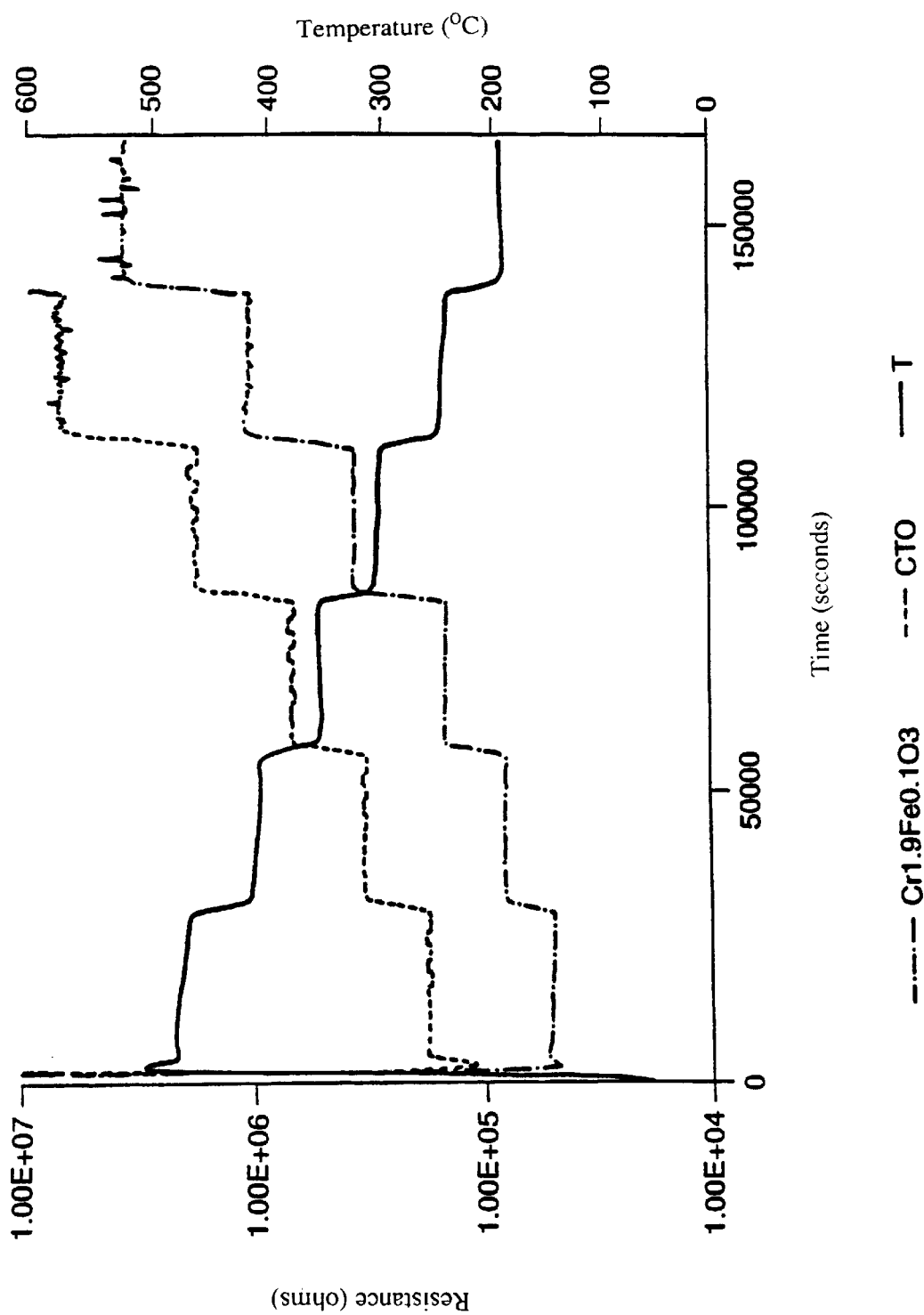
Figure 6:
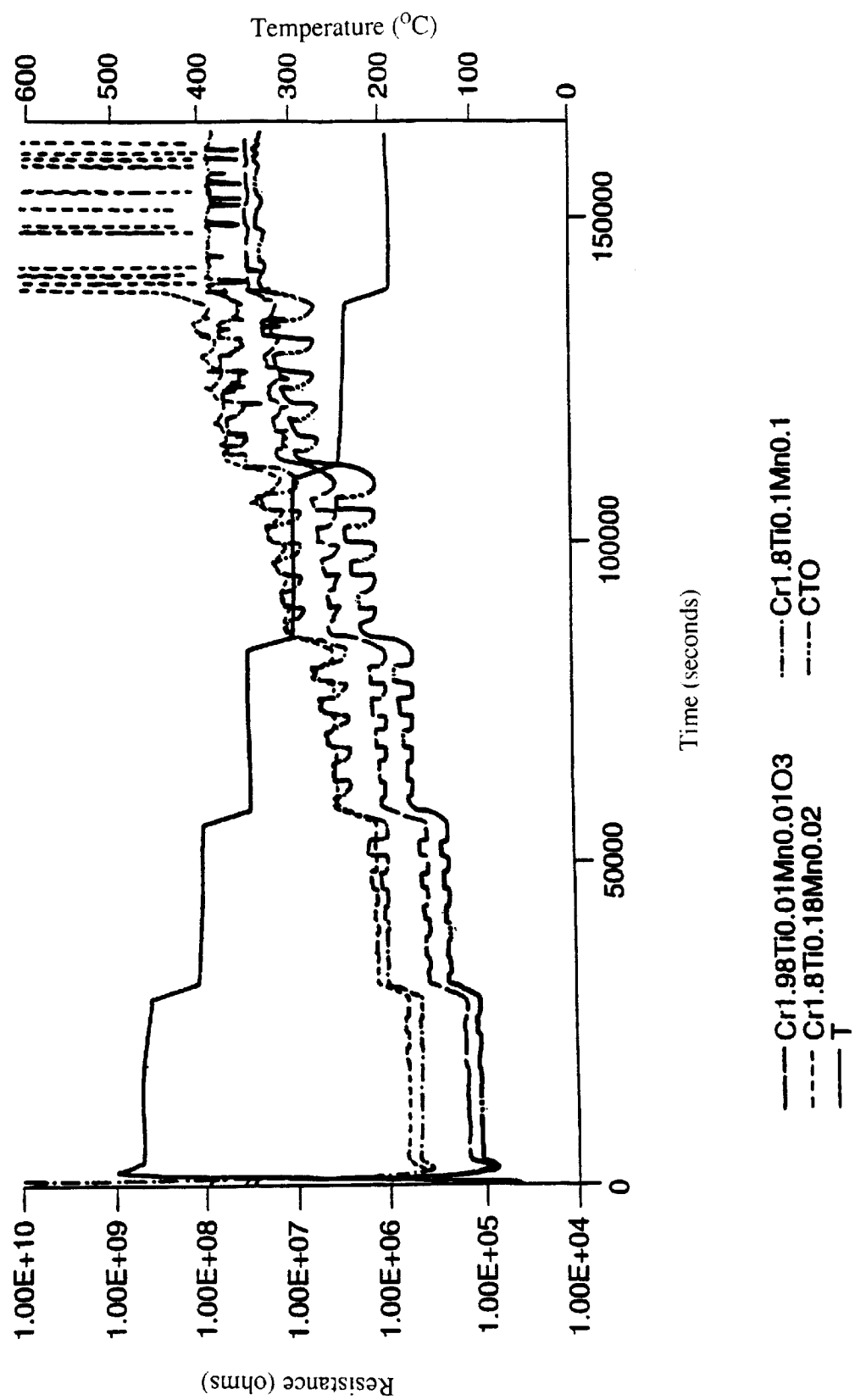
FIGS. 6 and 7 show the responses of chromium manganese oxide and chromium titanium oxide to CO at various concentrations, and water at various relative humidities, respectively.
Figure 7:
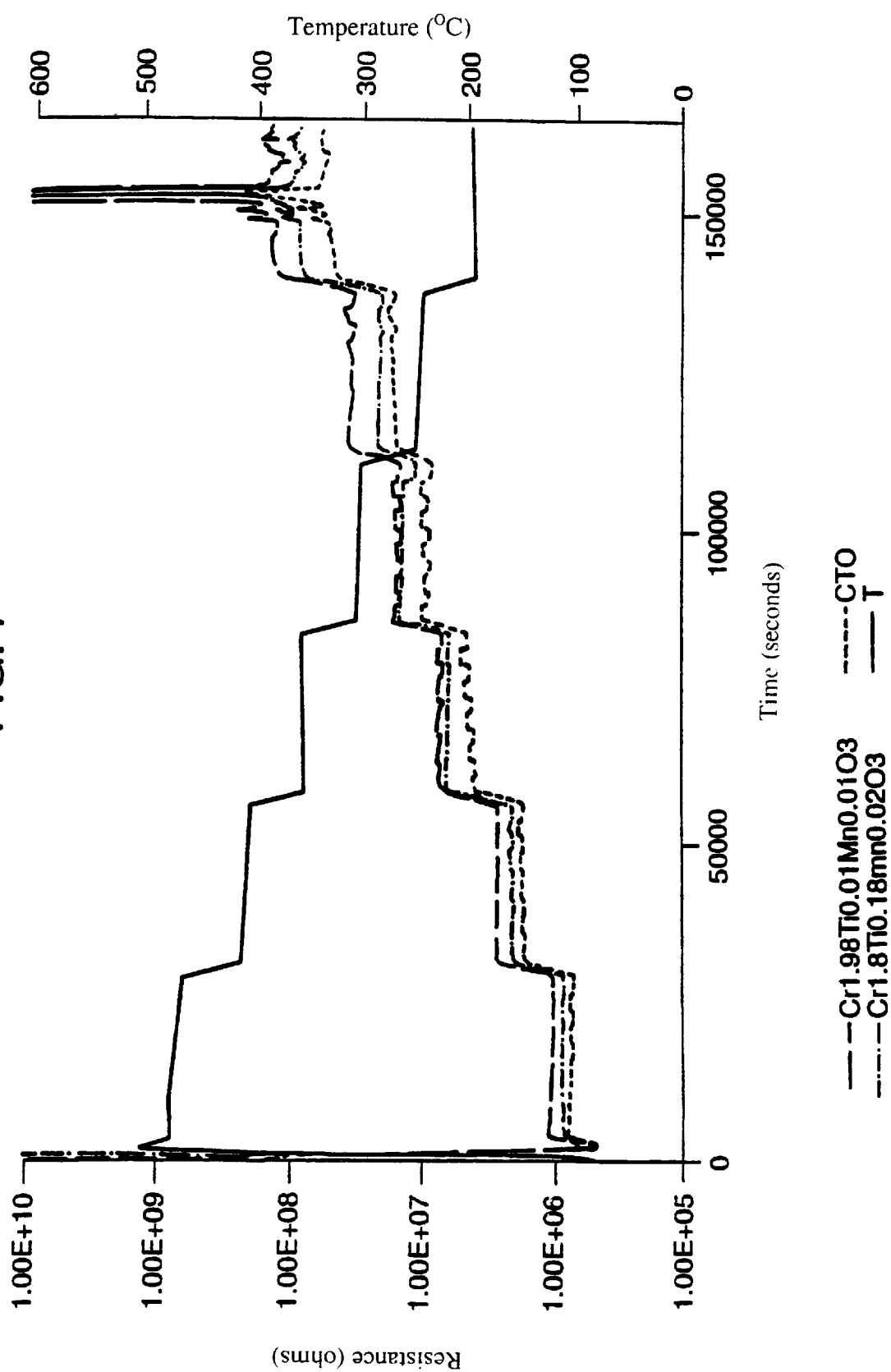
Figure 8:
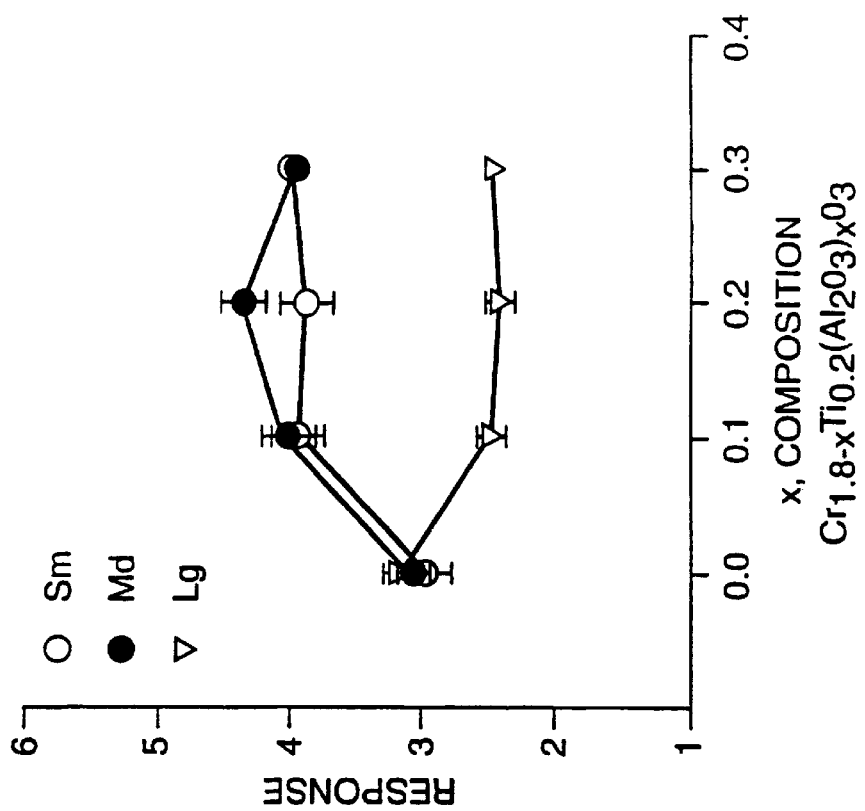
FIGS. 8 to 11 are graphs showing the responses of chromium titanium aluminium oxide, when in the form of a multiple electrode sensor, to CO, ethanol, $NH_3$ and water at 95% relative humidity (20° C.) respectively.
Figure 9:
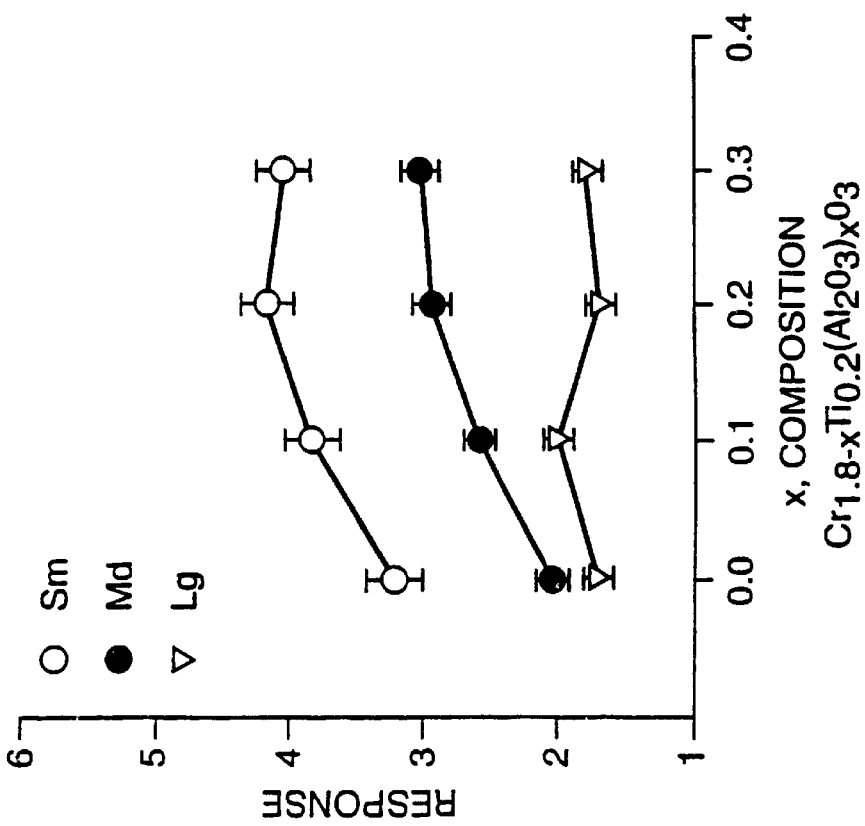
Figure 10:
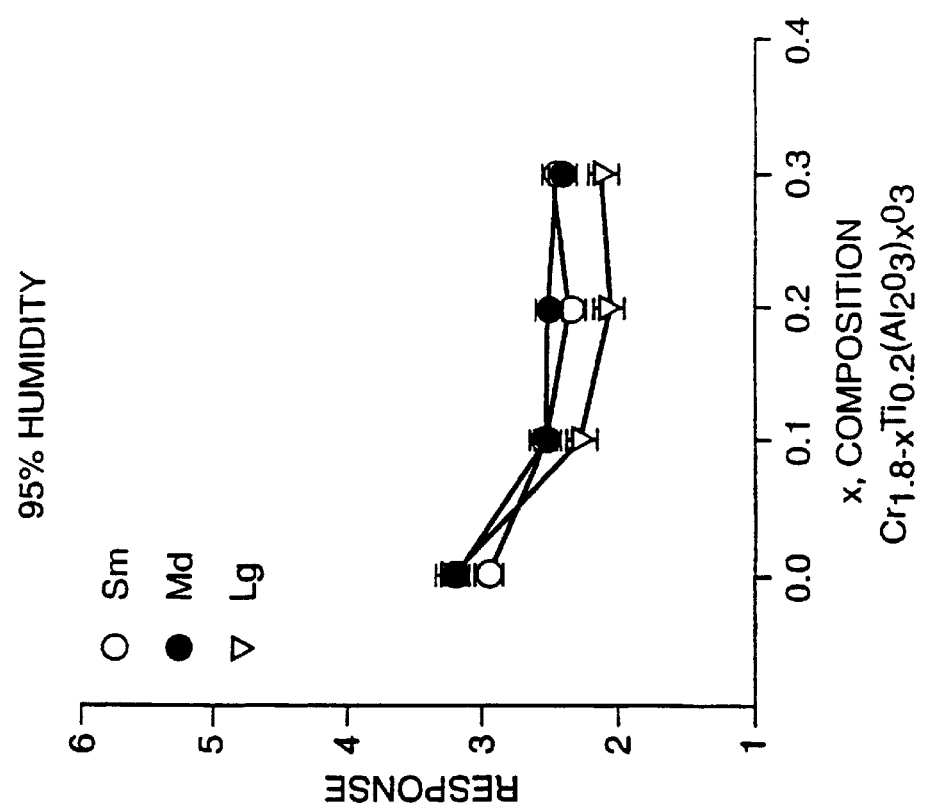

In FIGS. 1 to 3, the response $R/R_0$ is the ratio of the resistance of the pellet in CO or water to the resistance without CO or water.

FIG. 1 shows the response of pellets of the above 5 materials, held at 350° C., to increasing concentrations of carbon monoxide. All 5 showed a response increasing with concentration, the response by CTMO being highest and CMO lowest.

FIG. 2 shows the response of pellets of the above 5 materials to 500 ppm carbon monoxide, when the pellets were held at various temperatures.

FIG. 3 shows the response of pellets of the above 5 materials to water at 20% relative humidity, when the pellets were held at various temperatures. CTFO had virtually no response.

In FIGS. 4 to 7 the response on the left-hand y-axis is the resistance of the pellets in ohms plotted against time in seconds, for the pellets held at various temperatures. The temperature is shown on the right-hand y-axis. At each temperature the pellets were subjected successively to CO at a concentration of 100/200/500/1000/2000 ppm, and to water at 1/2/5/10/20% relative humidity (20° C.).

All materials indicated showed some degree of response to carbon monoxide and water, although the response of $Cr_{1.9}Fe_{0.1}O_3$ to water was very small.

Figure 11:
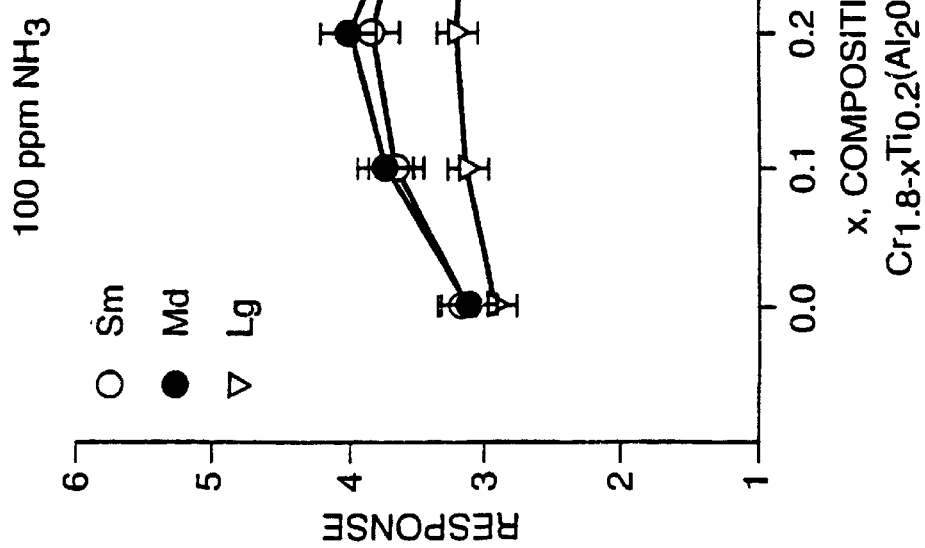

For the results shown in FIGS. 8 to 11, multi-electrode gas sensors were formed for the material $Cr_{1.8-x}Ti_{0.2}(Al_2O_3)_xO_3$, where x=0.1 to 0.3. (Multi-electrode gas sensors are well known, for example see EP-B-0591240). The response, $R/R_0$, was measured for electrodes with a small gap (Sm), medium gap (Md), and large gap (Lg). The sensors were operated at 350° C. for four test gases: 1000 ppm CO (FIG. 8), 10 ppm ethanol (FIG. 9), 100 ppm $NH_3$ (FIG. 10), and water at 95% relative humidity (FIG. 11).

What is claimed is:

1. A method comprising exposing a solid-state composition to a gas, wherein the composition is:
   (1) a ternary oxide of the formula $Cr_{2-x}(M1_zM2_{1-z})_xO_3$ with M1=Fe or Mn, M2=Fe, Mn or Al, $0.005 \leq x \leq 1.95$ and $0.005 \leq z \leq 0.995$; or
   (2) a ternary oxide of the formula $Cr_{2-x}(M1_zM2_{1-z})_xO_3$ with M1=Fe or Mn, M2=Ti and $0.005 \leq x \leq 1.95$, $0.005 \leq z \leq 0.45$; or
   (3) a quaternary or quinternary oxide of the formula $Cr_{2-x}((M1_aM2_bM3_c)_zM4_{1-z})_xO_3$ with M1=Fe, M2=Mn, M3=Al and M4=Ti, and $0 \leq a,b,c \leq 1$, $0.005 \leq x \leq 1.95$, and $0.005 \leq z \leq 0.45$;

and sensing an electrical response of said composition to said gas.

2. The method of claim 1 wherein the composition has the formula $Cr_{1.8}Ti_{0.18}Mn_{0.02}O_3$.

3. The method of claim 1 wherein the gas is carbon monoxide in air.

4. The method of claim 1 wherein the composition is a ternary oxide of the formula $Cr_{2-x}(M1_zM2_{1-z})_xO_3$ with M1=Fe or Mn, M2=Fe, Mn or Al, $0.005 \leq x \leq 1.95$ and $0.005 \leq z \leq 0.995$.

5. The method of claim 1 wherein the composition is a ternary oxide of the formula $Cr_{2-x}(M1_zM2_{1-z})_xO_3$ with M1=Fe or Mn, M2=Ti and $0.005 \leq x \leq 1.95$, $0.005 \leq z \leq 0.45$.

6. The method of claim 1 wherein the composition is a quaternary or quinternary oxide of the formula $Cr_{2-x}((M1_aM2_bM3_c)_zM4_{1-z})_xO_3$ with M1=Fe, M2=Mn, M3=Al and M4=Ti, and $0 \leq a,b,c \leq 1$, $0.005 \leq x \leq 1.95$, and $0.005 \leq z \leq 0.45$.

7. The method of claim 1 wherein the electrical response is a change in resistance.

8. The method of claim 1 wherein the electrical response is in proportion to a concentration of the gas.

9. A gas sensor comprising:
   (1) a ternary oxide of the formula $Cr_{2-x}(M1_zM2_{1-z})_xO_3$ with M1=Fe or Mn, M2=Fe, Mn or Al, $0.005 \leq x \leq 1.95$ and $0.005 \leq z \leq 0.995$; or
   (2) a ternary oxide of the formula $Cr_{2-x}(M1_zM2_{1-z})_xO_3$ with M1=Fe or Mn, M2=Ti and $0.005 \leq x \leq 1.95$, $0.005 \leq z \leq 0.45$; or
   (3) a quaternary or quinternary oxide of the formula $Cr_{2-x}((M1_aM2_bM3_c)_zM4_{1-z})_xO_3$ with M1=Fe, M2=Mn, M3=Al and M4=Ti, and $0 \leq a,b,c \leq 1$, $0.005 \leq x \leq 1.95$, and $0.005 \leq z \leq 0.45$.

10. A method comprising exposing a solid-state composition to a gas, wherein the composition is a ternary oxide of formula $Cr_{1.8}Ti_{0.1}Mn_{0.1}O_3$, $Cr_{1.8}Ti_{0.1}Fe_{0.1}O_3$, or $Cr_{1.98}Ti_{0.01}Mn_{0.01}O_3$; and sensing an electrical response of said composition to said gas.

* * * * *